(12) United States Patent
Yu et al.

(10) Patent No.: US 9,433,351 B2
(45) Date of Patent: Sep. 6, 2016

(54) TRI MODAL SPECTROSCOPIC IMAGING

(75) Inventors: Chung-Chieh Yu, Tuscon, AZ (US);
Condon Lau, Cambridge, MA (US);
Stephen Fulghum, Marblehead, MA (US); Christopher Fang-yen, Somerville, MA (US); Ramachandra Dasari, Shererville, IN (US); Michael Feld, Jamaica Plain, MA (US); David Feld, legal representative, Newark, CA (US); Alison Hearn, legal representative, Jamaica Plain, MA (US); Jonathan Feld, legal representative, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/464,578

(22) Filed: May 4, 2012

(65) Prior Publication Data
US 2012/0259228 A1   Oct. 11, 2012

Related U.S. Application Data

(63) Continuation of application No. 11/492,298, filed on Jul. 25, 2006, now abandoned.

(60) Provisional application No. 60/702,246, filed on Jul. 25, 2005.

(51) Int. Cl.
| A61B 6/00 | (2006.01) |
| A61B 5/00 | (2006.01) |
| G01J 3/02 | (2006.01) |
| G01J 3/10 | (2006.01) |
| G01J 3/32 | (2006.01) |
| G01N 21/47 | (2006.01) |
| G01N 21/49 | (2006.01) |

(52) U.S. Cl.
CPC .......... *A61B 5/0059* (2013.01); *A61B 5/0066* (2013.01); *G01J 3/02* (2013.01); *G01J 3/0224* (2013.01); *G01J 3/0229* (2013.01); *G01J 3/10* (2013.01); *G01J 3/32* (2013.01); *G01N 21/4738* (2013.01); *G01N 21/49* (2013.01); *G01N 2021/4733* (2013.01)

(58) Field of Classification Search
CPC ..... A61B 5/0059; A61B 5/0066; G01J 3/02; G01J 3/0224; G01J 3/0229; G01J 3/10; G01J 3/32; G01N 2021/4733; G01N 21/4738; G01N 21/49

See application file for complete search history.

(56) References Cited

U.S. PATENT DOCUMENTS

| 5,719,399 | A | * | 2/1998 | Alfano et al. | 250/341.3 |
| 5,936,739 | A | * | 8/1999 | Cameron et al. | 356/441 |
| 6,219,566 | B1 | * | 4/2001 | Weersink et al. | 600/317 |
| 6,370,422 | B1 | * | 4/2002 | Richards-Kortum et al. | 600/478 |
| 6,766,184 | B2 | * | 7/2004 | Utzinger et al. | 600/407 |
| 7,006,676 | B1 | * | 2/2006 | Zeylikovich et al. | 382/131 |
| 2002/0037149 | A1 | * | 3/2002 | Chen | 385/147 |
| 2003/0232445 | A1 | * | 12/2003 | Fulghum, Jr. | 436/63 |
| 2004/0087844 | A1 | * | 5/2004 | Yen | 600/319 |
| 2005/0020926 | A1 | * | 1/2005 | Wiklof et al. | 600/476 |
| 2005/0211872 | A1 | * | 9/2005 | Kawano et al. | 250/201.3 |
| 2006/0186325 | A1 | * | 8/2006 | Johnston et al. | 250/234 |

* cited by examiner

*Primary Examiner* — Ruth S Smith

(74) *Attorney, Agent, or Firm* — McCarter & English, LLP

(57) ABSTRACT

The present invention relates to a spectroscopic imaging system using autofluorescence and reflectance images to diagnose tissue. A preferred embodiment of the invention uses a plurality of light sources to illuminate a tissue region to provide the fluorescence and reflectance images, respectively.

28 Claims, 14 Drawing Sheets

LSS Imaging System

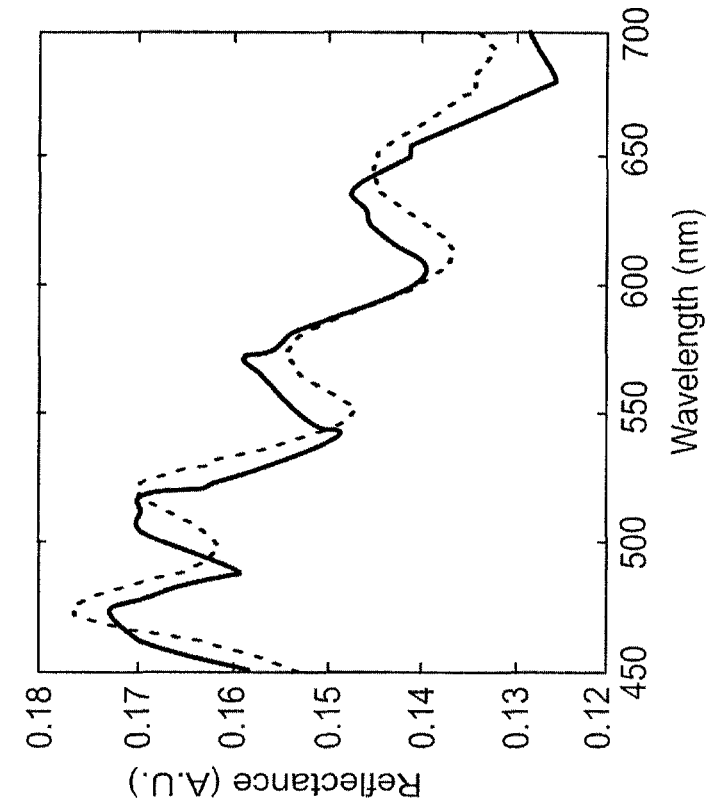
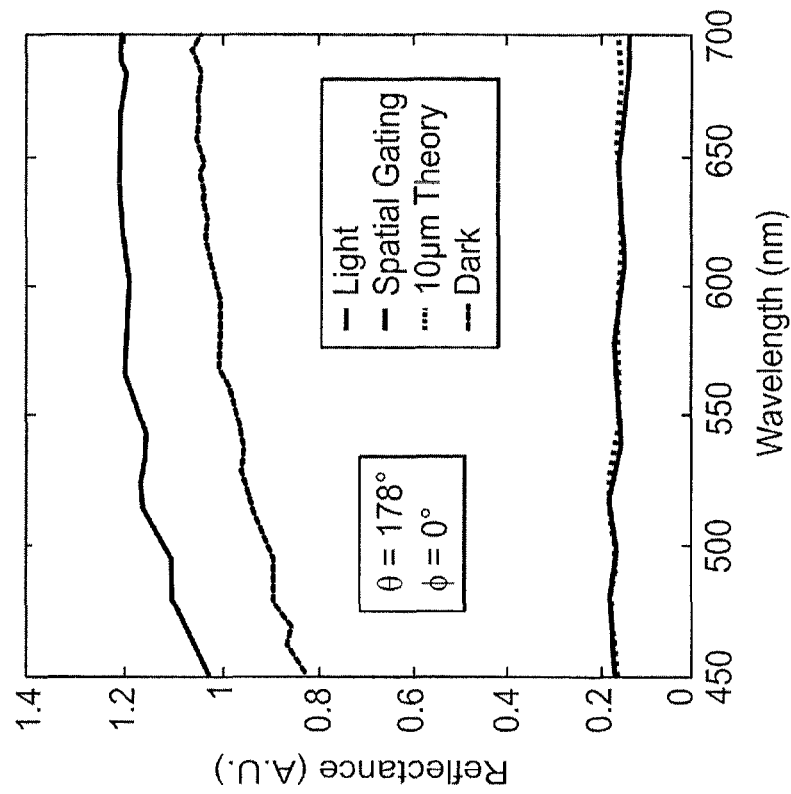
FIG. 8A
FIG. 8B

Spectral intensity variation of φ = 0° and φ = 90° lobes

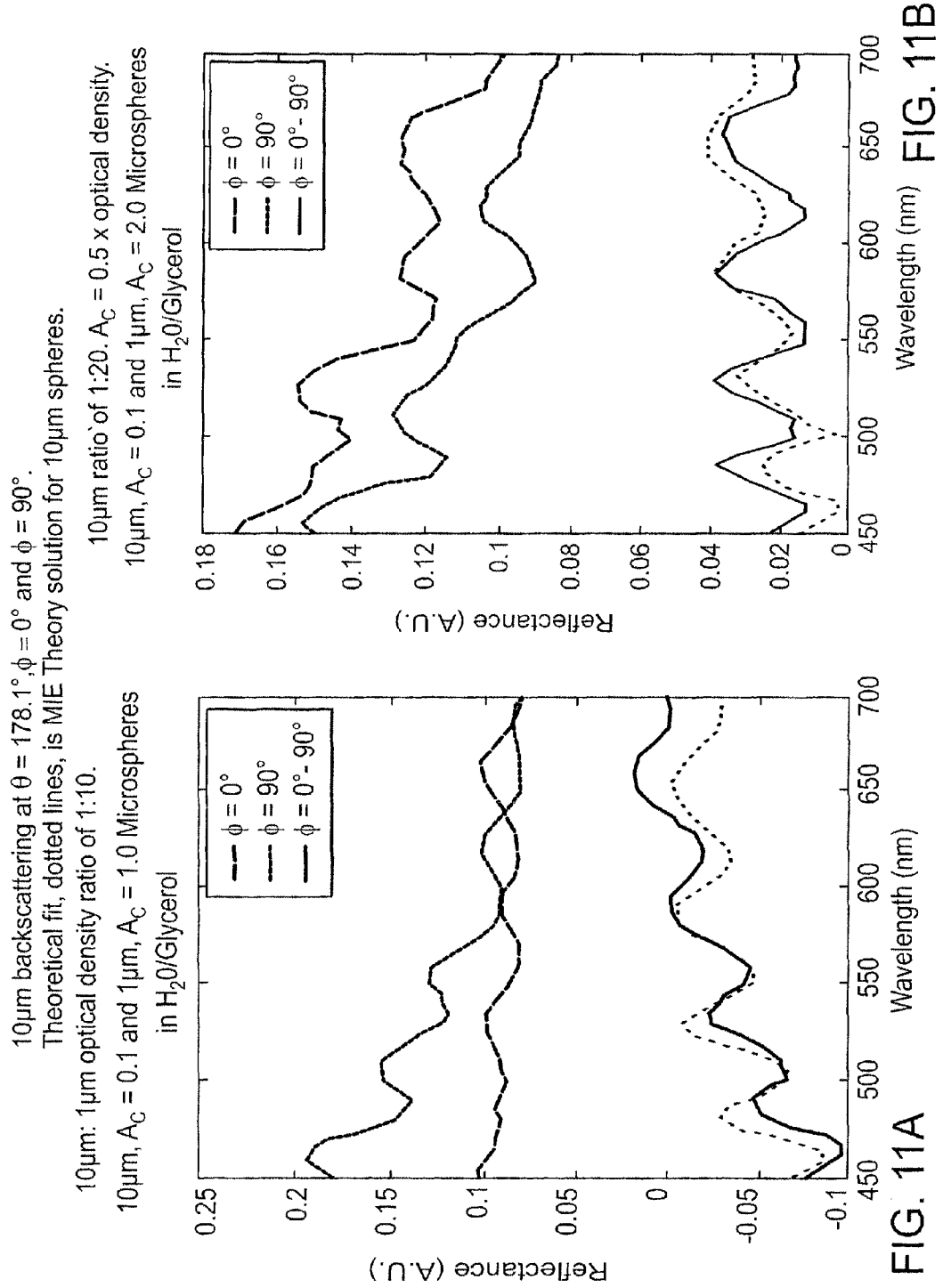

TRI MODAL SPECTROSCOPIC IMAGING

CROSS REFERENCE TO RELATED APPLICATION

This continuation application claims the priority of U.S. application Ser. No. 11/492,298 filed Jul. 25, 2006 now abandoned and U.S. Provisional Application No. 60/702,246, filed Jul. 25, 2005 entitled, TRI MODAL SPECTROSCOPIC IMAGING. The entire content of the above applications are being incorporated herein by reference.

GOVERNMENT SUPPORT

This invention was made with government support under Grant No. CA097966 and RR002594 awarded by National Institutes of Health. The government has certain rights in this invention.

BACKGROUND OF THE INVENTION

Cancer is the second leading cause of death in the world. Each year, cancer kills over 500 thousand people in the United States alone (National Cancer Institute). Current cancer diagnosis methods usually involve two medical procedures. The first procedure is a wide-area surveillance over the tissue, for example: mammogram, colposcopy, palpation, or visual examination. When warning signs are present, biopsy is performed on the suspicious tissue sites. However, many forms of precancerous and early cancerous lesions are difficult to detect using these traditional surveillance procedures. Therefore, there is a need for wide-area surveillance systems capable of precancer detection.

Medical imaging modalities such as mammography and colposcopy have proven vitally important for cancer diagnosis. So far, the majority of imaging modalities focus on tissue structure or anatomy, which is not sufficient for detecting precancers at their earliest stages. Biochemical and subcellular morphological changes have been shown to accompany precancer development. Thus, it is most beneficial to develop new cancer imaging modalities that provide tissue biochemical and morphological information. Several new optical imaging modalities show great promise:

Confocal microscopy eliminates multiple scattering in turbid samples, producing thin section images with high resolution and contrast. The images produced are due to light scattered backwards at interfaces of different refractive index. Multiple scattered light is rejected by means of a pinhole, which selects only light traveling in straight-line paths. The location and size of the pinhole, among other variables, determine the depth and lateral resolution of the system.

Optical coherence tomography (OCT) utilizes the coherence properties of light to obtain cross sectional images of scattering media such as living tissue. This technique employs low coherence light (i.e. light with a short coherence length) in a Michelson interferometer. The specimen is placed at the end of the sample arm. Back-scattered light is combined with light returning from the mirror in the reference arm. Constructive interference occurs only when the distance to a scattering interface in the sample matches that to the reference mirror to within the coherence length. Depth is probed by scanning the reference mirror position and detecting the envelope of the interference signal. Cross-sectional images can be built up from multiple axial scans at different transverse positions in the sample. As with confocal microscopy, image formation is again due to refractive index change.

Several groups have used polarized light to image superficial tissues including using polarized light to enhance contrast in skin images by separating the specular and multiple-scattered components of light emerging from the skin surface or polarized gating can enhance the images of surface and sub-surface structures in biological tissues.

Fluorescence is induced by the excitation of fluorophores in the tissue, usually with blue or ultraviolet (UV) light. Therefore, fluorescence contains information about fluorophore concentration in the tissue. Two-photon microscopy (TPM) is capable of imaging fluorophores deep within a tissue sample. Tissue auto-fluorescence has also been used to detect neoplastic growths in-vivo.

Medical imaging modalities for precancer diagnosis can also employ spectroscopy. Fluorescence spectroscopy imaging systems have been used for detecting cervical intraepithelial neoplasia and combined fluorescence and reflectance spectroscopy methods are complementary for cancer diagnosis, making the use of the two techniques together more diagnostic than the use of either method separately.

SUMMARY OF THE INVENTION

Tri modal spectroscopy (TMS) can combine spectroscopic techniques to gain biochemical, structural, and morphological information simultaneously. The present invention uses both fluorescence and reflectance imaging systems and methods for both in vivo and ex-vivo measurements. Intrinsic fluorescence spectroscopy (IFS) is used, for example, to obtain relative concentrations of fluorophores (e.g. NADH and collagen). Diffuse reflectance spectroscopy (DRS) provides information about the morphology and biochemistry of the stromal tissue and values of the absorption and reduced scattering coefficients, $\mu_a(\lambda)$ and $\mu_s(\lambda)$. Light scattering spectroscopy (LSS) determines nuclear size, density, and distribution.

TMS has been implemented previously into a single point clinical instrument, to perform early cancer detection in-vivo. Three organ types have been measured including the esophagus, cervix, and oral cavity. The results demonstrated that TMS offered higher sensitivity and specificity than any one spectroscopic technique alone.

Ex-vivo tissue measurements performed with LSS imaging system and measurements conducted using tri-modal spectroscopy implemented in a single point instrument showed LSS imaging and TMS can be used for precancer diagnosis. Implementing TMS into an imaging system provides the advantage for screening larger regions of the body at faster speeds. The TMS imaging instrument can improve the sensitivity and specificity of cancer diagnosis with wide-area imaging systems while maintaining their abilities to provide real-time, non-invasive diagnosis.

Note that propagation of diffusely scattered light renders localized diagnosis more difficult because reflectance detected in one area of the tissue may carry contributions from other areas. Another challenge is to isolate single backscattering, diffuse reflectance, and intrinsic fluorescence so each component can be analyzed separately. The methods separate single scattering from diffuse reflectance and discriminate the light scattering spectrum of certain size scatterers from that of others.

A preferred embodiment of the invention uses angular gating for light scattering spectroscopy. This embodiment utilizes the measurement of at least two reflectance spectra at two azimuthal angles to characterize tissue.

BRIEF DESCRIPTION OF THE DRAWINGS

FIGS. 8a and 8b are measured spectra;
FIGS. 11a and 11b are backscattering measurements.

DETAILED DESCRIPTION OF THE INVENTION

Figure 1:
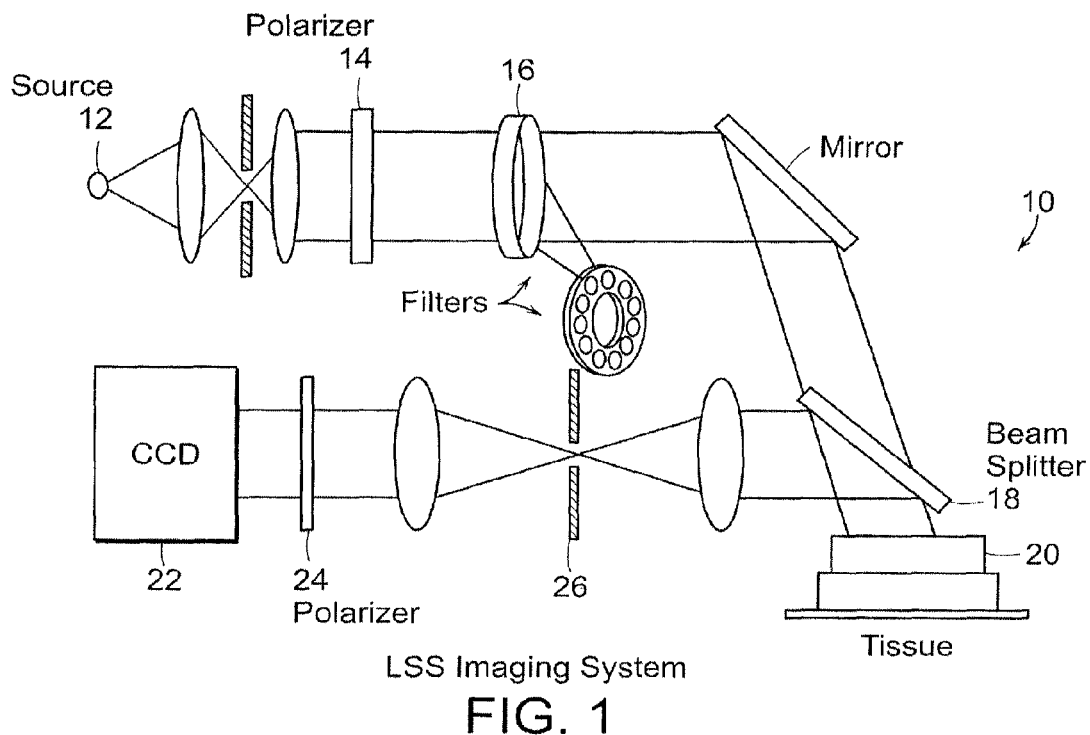
FIG. 1 is an LSS imaging system.

A spectroscopic imaging system in accordance with a preferred embodiment of the invention can be for precancer detection over a relatively large 1.3 cm by 1.3 cm area, for example. FIG. 1 depicts such a system 10. A 75 W xenon arc lamp light source 12 (Oriel, Inc.) illuminates the tissue 20. The light is collimated with half angle 0.5°, polarized 14, and transmitted through one of 11 narrow-band (4 nm) filters 16 (Edmund Scientific) to select the wavelength in the range 450-700 nm. The reflectance from the tissue is diverted by the beamsplitter 18 to a 4f imaging system 22 that images the illuminated surface of the sample 1:1 onto the CCD (Princeton Instruments, Inc.). The CCD consists of 512×512 pixel array with pixel size 25×25 microns. A polarizer 24 along the collection path selects the polarization state of the collected light. An iris 26 positioned at the center of the 4f lens system collects only light scattered into a solid angle corresponding to a half angle of 0.5°. For each sample, two different reflectance spectra are measured, one with collection polarization parallel to that of excitation, and the other with perpendicular collection polarization. The polarization gating technique is used to extract the single backscattering spectrum by subtracting perpendicular spectrum from the parallel spectrum.

TABLE C.1

Comparison of the values of the mean nuclear diameters and standard deviations of nuclear sizes in the colon adenoma of FIG. C.2 and surrounding non-dysplastic epithelium measured with LSS and using standard morphometry of the stained tissues.

|   |   | Morphometry | | LSS | |
|---|---|---|---|---|---|
| Normal mucosa | Mean nuclear diameter and standard error of measurement, μm | 5.60 | 0.20 | 5.70 | 0.13 |
|   | Standard deviation of nuclear diameters, μm | 1.01 | | 0.82 | |

TABLE C.1-continued

Comparison of the values of the mean nuclear diameters and standard deviations of nuclear sizes in the colon adenoma of FIG. C.2 and surrounding non-dysplastic epithelium measured with LSS and using standard morphometry of the stained tissues.

|   |   | Morphometry | | LSS | |
|---|---|---|---|---|---|
| Adenoma | Mean nuclear diameter and standard error of measurement, μm | 7.44 | 0.23 | 7.67 | 0.40 |
|   | Standard deviation of nuclear diameters, μm | 1.59 | | 2.19 | |

Experiments were conducted on physical tissue models of microspheres on a diffusive medium, monolayers of T84 tumor colon cells, and ex-vivo colon tissue. From experiments with physical models and cells, the accuracy of measuring size and relative index of refraction are 25 nm and 0.001 respectively were established.

Figure 2:
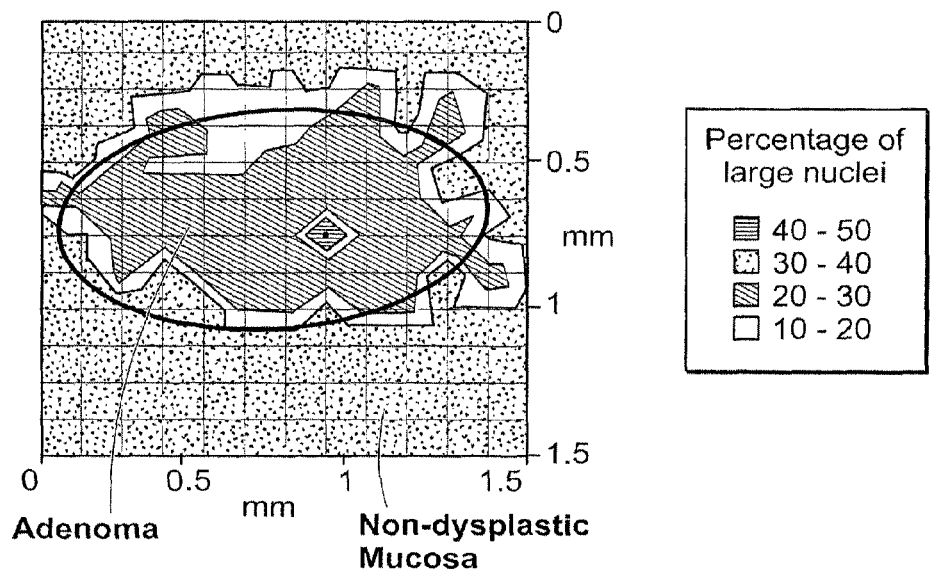
FIG. 2 is an image of a tissue sample.

LSS measurements of cancerous ex-vivo colon tissue were used to test nuclear sizing. FIG. 2 shows a coded image indicating different percentages of enlarged nuclei (greater than 10 μm in diameter). The light scattering measurements were compared with morphometry measurements done under a microscope. The results are compared on Table 1. Adenomas demonstrate clear nuclear enlargement over normal mucosa and size distribution is also more varied. Nuclear enlargement and variation are strong indicators of dysplasia. LSS results agree well with those of microscopy and wide area imaging has been demonstrated to work very effectively.

Using a plurality of excitation and emission wavelengths (fastEEM) measurements for non-invasive detection of dysplasia in three organs: uterine cervix, esophagus and oral cavity.

TABLE C.2

Performance of different spectroscopic techniques for separating SILs from non-SILs

|   | Biopsied non-SILs* vs SILs (%) | | Non-SILs† vs SILs (%) | |
|---|---|---|---|---|
| Technique | Sensitivity | Specificity | Sensitivity | Specificity |
| IFS | 62 | 67 | 62 | 92 |
| DRS | 69 | 57 | 62 | 82 |
| LSS | 77 | 71 | 77 | 83 |
| TMS | 92 | 71 | 92 | 90 |

*Biopsied non-SILs include 21 colposcopically abnormal biopsied sites that were classified as MSE (5/21 sites) or SQM (16/21) sites.
†Non-SILs in this case include 50 colposcopically normal sites and 21 biopsied sites that were classified as SQM or MSE Table 2 presents results from an extensive in-vivo study of uterine cervix dysplasia using the fastEEM. IFS, DRS, and LSS alone separated biopsied squamous intraepithelial lesions (SIL) from the biopsied non-SILs and the biopsied SILs from all spectroscopically examined non-SILs with sensitivities and specificities shown in the first 3 rows. TMS performed the same separations with sensitivities and specificities shown on row 4. The results show TMS offers better sensitivity and specificity than any one spectral modality alone.

Figure 3:
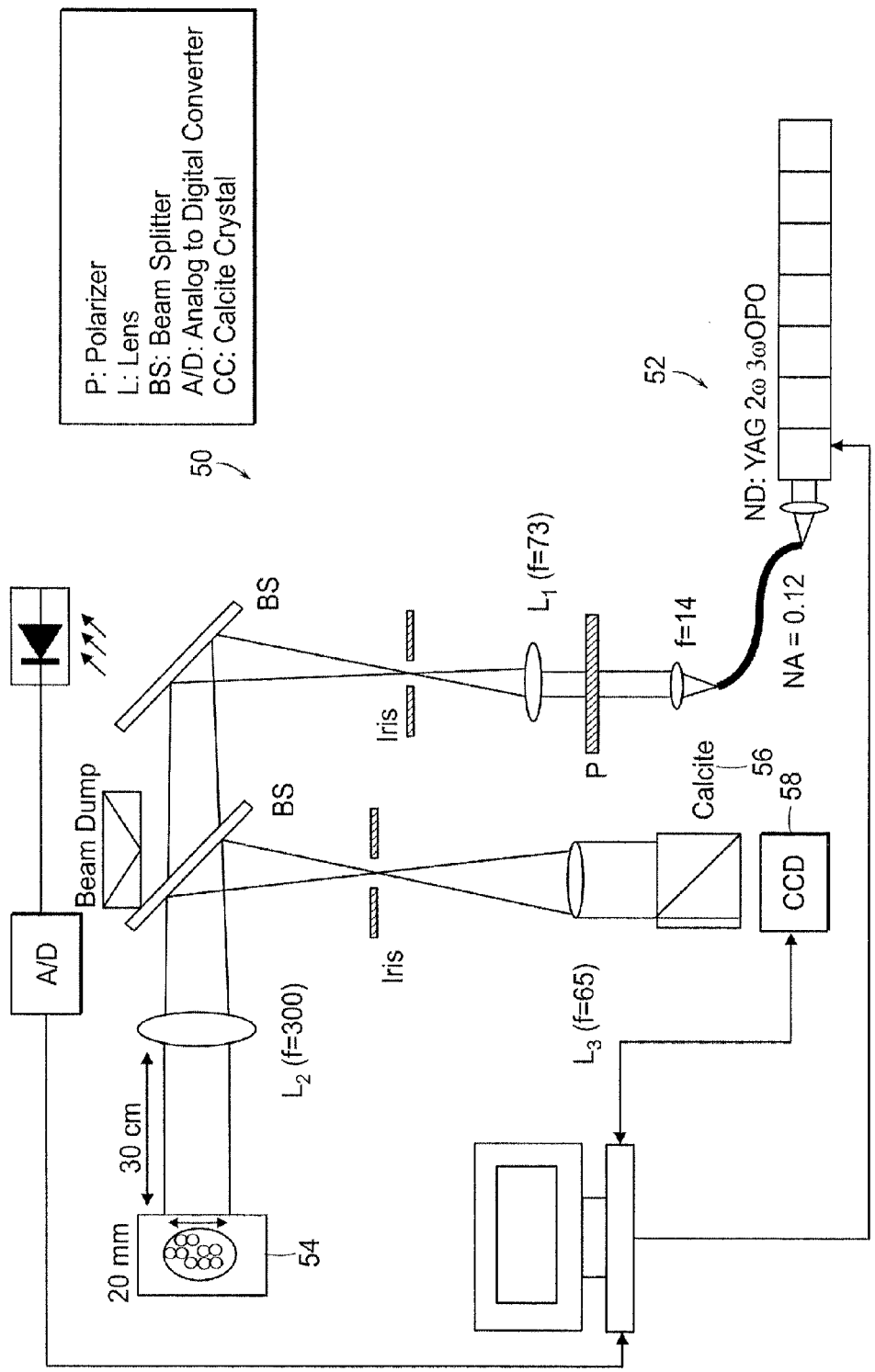
FIG. 3 is a LSS imaging system.

FIG. 3 is a system for LSS imaging 50. The light source 52 is a 20 Hz Q-switched ND:YAG Laser (Opotek) pumped optical parametric oscillator (OPO). Light is coupled into a fiber (Fiberguide Industries, d=1 mm, NA=0.12) by a focusing lens (f=25 mm) and transmitted to the collimating lens (f=14 mm). The excitation is expanded 1:4 onto the sample 54 through a 4f system ($L_1$ and $L_2$). The iris on the excitation path limits the excitation collimation to half-angle of 0.5 degrees. Polarizer P defines the excitation polarization. Light scattered at θ=180° from the sample travels along the excitation path prior to being redirected by the beam splitter and imaged through another 4f system ($L_2$ and $L_3$) onto the 12-bit CCD (Roper Scientific CoolSNAP HQ, 1392×1040 pixel array, pixel size 6.5×6.5 microns). The image is demagnified 5:1 by the optics. The iris on the collection path restricts the angular span of the backscattered light collected to ±0.5 degrees. A calcite crystal 56 splits the collected light into parallel and perpendicular polarizations for polarization gating [Backman 1999].

Control and data acquisition have been automated using software developed with National Instruments LabView 6.1. Each set of spectral data is acquired with excitation wavelength stepped from 470 nm to 670 nm in 2 nm increments. The CCD 58 can be divided into 30 pixel by 30 pixel areas. Each area corresponds to ~1 mm² on the sample. Measured spectra from each area, $I_{m,\|}(\lambda_i,x,y)$ (parallel) and $I_{m,\perp}(\lambda_i,x,y)$ (perpendicular) for (i=1, 2 . . . 100, 101), are the averaged spectra over all pixels in that area. One image is acquired for each excitation wavelength. Only one run is required to measure both parallel and perpendicular spectra because the calcite crystal divides the polarization. This halves data-acquisition time. For each sample, we also measure spectra with spectralon, $I_{s,\|}(\lambda_i,x,y)$ and $I_{s,\perp}(\lambda_i,x,y)$, for normalization. Normalization accounts for spatial and spectral variations of the system. The $I_m$'s are normalized by the $I_s$'s and mean centered to one:

$$\bar{I}_{m,\|}(\lambda_i, x, y) = \frac{\frac{I_{m,\|}(\lambda_i, x, y)}{I_{s,\|}(\lambda_i, x, y)}}{\text{mean}\left(\frac{I_{m,\|}(\lambda_i, x, y)}{I_{s,\|}(\lambda_i, x, y)}\right)}$$

$$\bar{I}_{m,\perp}(\lambda_i, x, y) = \frac{\frac{I_{m,\perp}(\lambda_i, x, y)}{I_{s,\perp}(\lambda_i, x, y)}}{\text{mean}\left(\frac{I_{m,\perp}(\lambda_i, x, y)}{I_{s,\perp}(\lambda_i, x, y)}\right)}$$

The single scattering spectrum is obtained with polarization gating:

$$\bar{I}_{SS}(\lambda_i,x,y) = \bar{I}_{m,\|}(\lambda_i,x,y) - \bar{I}_{m,\perp}(\lambda_i,x,y)$$

Size information (mean and standard deviation) is extracted from the back scattering spectrum of each 1 mm² sample area. The extraction algorithm compares all $\bar{I}_{SS}(\lambda_i)$ to Mie Theory calculations of polarization gating, $$\bar{I}_{MIE}(\lambda_i, a, \delta) = \frac{I_{MIE,\|}(\lambda_i, a, \delta) - I_{MIE,\perp}(\lambda_i, a, \delta)}{\text{mean}(I_{MIE,\|}(\lambda_i, a, \delta) - I_{MIE,\perp}(\lambda_i, a, \delta))}.$$

This is the simulated single scattering spectra with mean centered to one. a is mean diameter and δ is standard deviation of size. For inhomogeneous samples, one $\bar{I}_{MIE}(\lambda_i,a,\delta)$ is computed for each area. The best least squares fit is found using fminsearch.m (Mathworks). The simulation program accounts for linewidth of the system, scattering angle measured, and relative index of refraction ($m = n_m/n_0$) between the sample ($n_m$) and the medium ($n_0$). Linewidth, scattering angle, and relative index of refraction strongly influence the measured backscattering spectrum.

Figure 4:
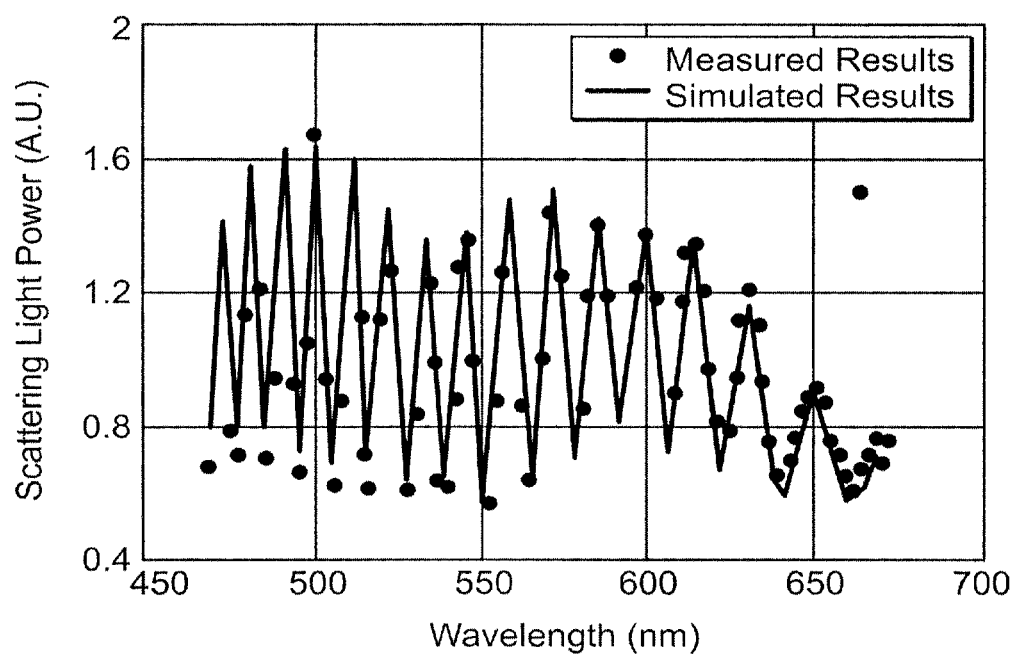
FIG. 4 is data from a system.

Systems and methods using a microscope cover slip sample containing 5 μm microspheres solution (Duke Scientific Corp.) accounted for the index of refraction spectral dependences of microspheres and water. FIG. 4 shows $\bar{I}_{SS}(\lambda_i,x,y)$ (dotted line) from one area of the sample. The simulated results are the best fit $\bar{I}_{MIE}(\lambda_i,a,\delta)$ (solid line). The agreement is excellent. Following the results obtained with 5 μm microspheres, we proceeded to validate the clinical prototype system with 5, 9, and 10 μm microspheres in water. Table 3 lists the measured size information (a, δ) for a randomly chosen area along side the manufacturer's specifications. The fits are excellent and the extracted parameters are within the manufacturing tolerances.

TABLE 3

Comparison of mean and standard deviation of diameter of polystyrene microspheres according to manufacturer specifications and as determined by the LSS imaging system

| | 5 μm Spheres | | 9 μm Spheres | | 10 μm Spheres | |
|---|---|---|---|---|---|---|
| | Mean | Stdev | Mean | Stdev | Mean | Stdev. |
| Manufacturer Spec. | 5.01 | 0.035 | 8.956 | 0.056 | 10.15 | 0.06 |
| LSS Imaging System | 5.011 | 0.0204 | 8.921 | 0.036 | 10.093 | 0.026 |

Figure 5:
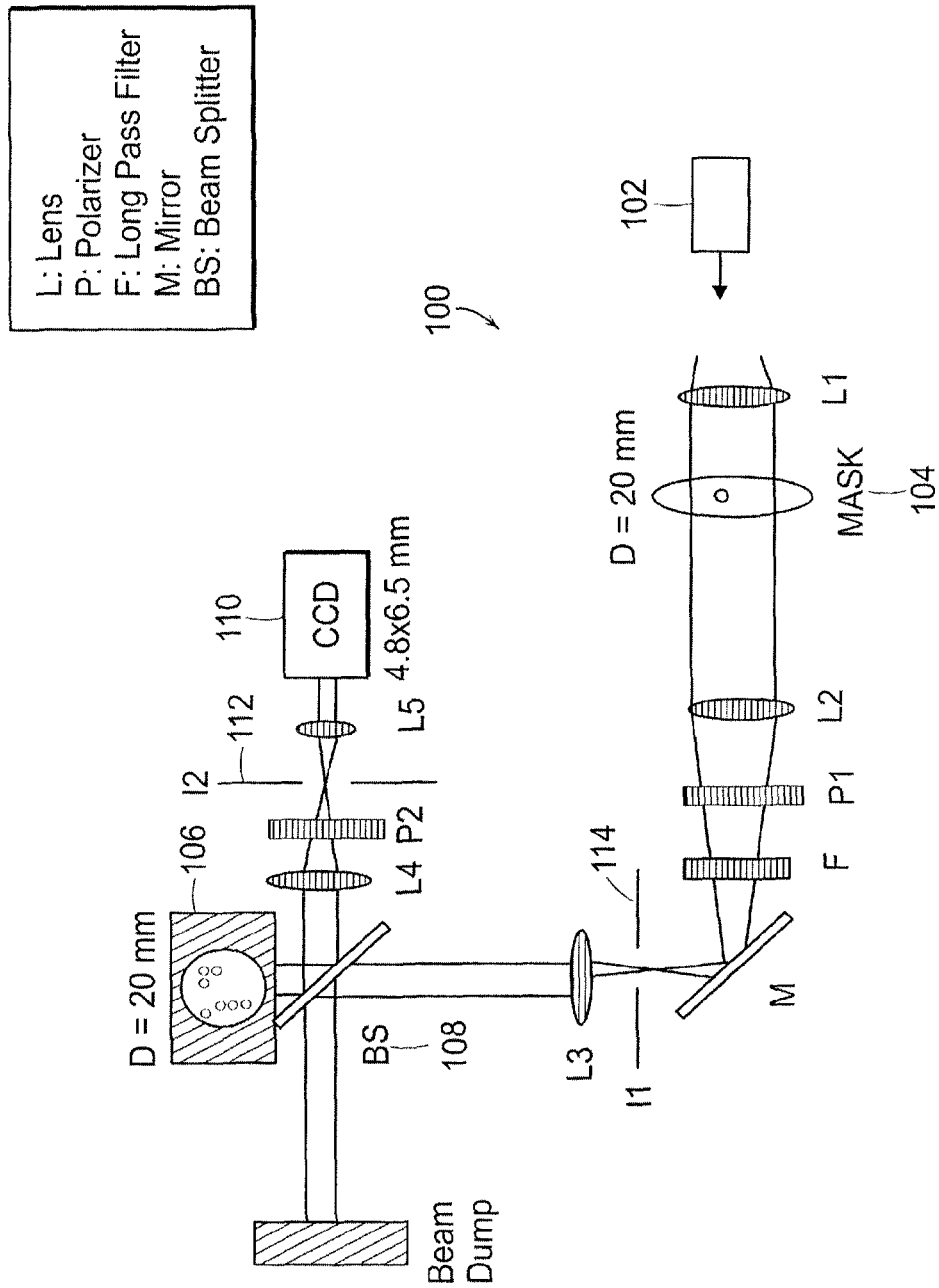
FIG. 5 is a TMS imaging system.

The schematic drawing of the system 100 for LSS including angular gating is shown in FIG. 5. The light source 102 is a 300W Xenon Arc Lamp (Oriel Thermo). A monochromator (Oriel Cornerstone) steps wavelength of excitation light with 10 nm FWHM spectral line width. The light is then collimated by L1. A 2 cm diameter patterned mask 104 is imaged 1:1 on to the sample by a 4-f system consisting of L2 and L3 with focal lengths of 40 cm. P1 defines the polarization of the excitation. A long pass filter removes light with wavelength below 385 nm. I1 limits the collimation of the excitation light to half angle of 0.5°. The reflectance from the sample 106 comes back along the path of the excitation before it is deflected by a beam splitter 108 into the collection path. Another 4-f system (L4 and L5) with 1:5 demagnification images the surface of the sample onto the CCD detector 110 (Photometrics Sensys, 768×512 pixel array, pixel size 9×9 microns). The iris 112 on the collection path restricts the angular span of collected backscattered light to ±0.5 degrees.

Figure 6:
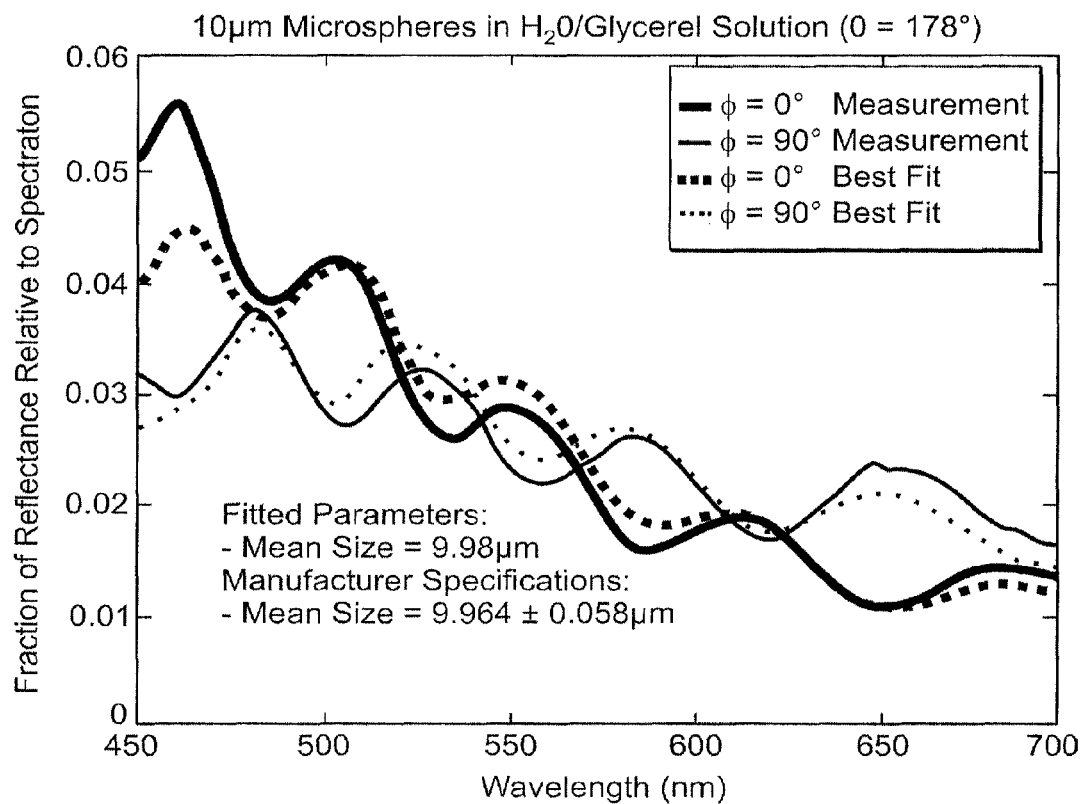
FIG. 6 is a graphical illustration of data collected on the system of FIG. 5.

The sample is illuminated by the excitation light with wavelength ranging from 450 nm to 700 nm in 5 nm increments. At each wavelength, the CCD acquires an image. Exposure time is varied for different sample types to utilize most of the 4096 counts available on each pixel. A spectrum, $I_m(\lambda_i,x,y)$ for (i=1, 2 . . . 50, 51), is obtained for each unit area, 20 pixel×20 pixel, on the CCD by plotting the recorded intensities at the different wavelength images. For each spectrum from a sample we measure a corresponding spectrum is measured, $I_s(\lambda_i,x,y)$, for normalization purposes by replacing the sample with a broadband dielectric mirror (Thorlabs, Inc.). This accounts for spectral and spatial variations of our system because reflectance from the mirror is above 99% over the entire spectrum. Measured reflectance spectra were obtained from a 1 mm thick, 1" diameter solution of 10 μm microspheres (Duke Scientific Corp.) immersed in a density matching fluid (80% water and 20% glycerol). The standard deviation of the microspheres' diameter was 0.058 μm. The optical thickness of the microspheres, λ, was about 0.2. Spectra were measured for backscattering angles θ=178°, Φ=0° ($I_{m,0}(\lambda_i)$) and Φ=90° ($I_{m,90}(\lambda_i)$). FIG. 6 shows two of the normalized spectra, $I_{m,0}(\lambda_i,x,y)$ and $I_{m,90}(\lambda_i,x,y)$ (solid lines). Simulated results (dotted lines) were calculated using Mie theory.

Spatial gating is a powerful gating technique that separates light scattered by superficial layers of the sample from those photons that have traversed deeper sections.

Figure 7:
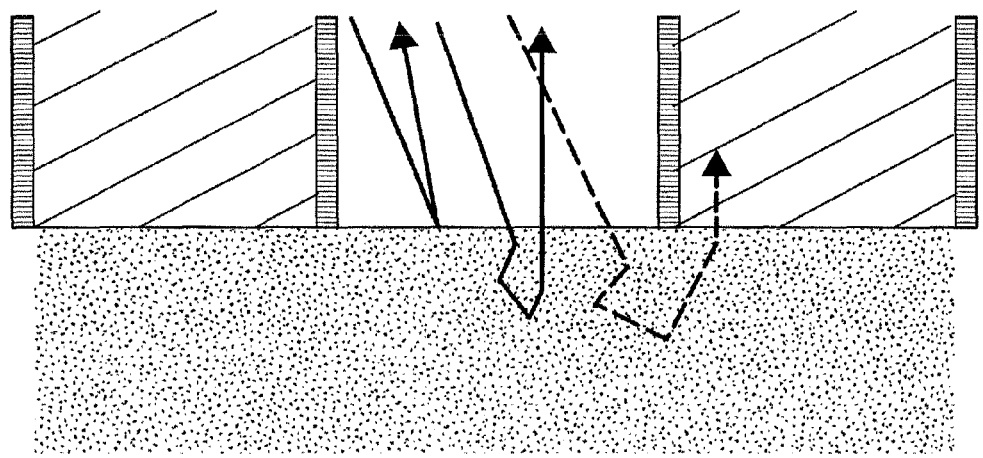
FIG. 7 is an illustration of scattering in tissue

Light reflected from the superficial layers have undergone few scattering events, including those that have scattered only once (single scattering intensity, $I_S$), while photons returning from deeper layers have scattered more (diffuse reflectance, $I_D$). FIG. 7 illustrates how spatial gating is used to separate single scattering from diffuse reflectance. The photons experiencing single backscattering enter and leave the sample from the same region. The photons experiencing multiple scatterings will enter and leave the sample either through the same region or a different one. The photons undergo neither single scattering nor diffuse reflectance. Photons that undergo more scattering events are increasingly likely to exit from a different region. Therefore, when the sample is imaged onto the CCD, single scattering will only appear in lighted areas while multiple scattering will appear in light and dark areas. Spatial gating uses a specific patterned mask in the system of FIG. 5. The mask consists of two parts: 1) a 1" iris 114 whose opening controls the size of the excitation and 2) a transparent glass with opaque regions providing a pattern that is imaged by a 4f system (L2 and L3 in FIG. 5) onto the sample to create dark regions. To obtain majority single scattering, measure the intensity in a lighted area and subtract measurements from the closest dark area as illustrated below:

Light area: $I_{light}=I_S+I_D$

Dark area: $I_{dark}=I_D$

Single scattering intensity: $I_{light}-I_{dark}=I_S$      (Equation 1)

Measurements with tissue phantoms validate spatial gating. The tissue phantoms are two-layer models designed to simulate epithelial cells on top of underlying tissue. Epithelial cell nuclei are approximated by 10 mucon microspheres (Duke Scientific Corp. and Polysciences Inc.) in the density-matching fluid used for system calibration. The optical density is about 0.2. Beneath the microspheres solution is 10% Intralipid. Intralipid models underlying tissue and it is diluted to have reduced scattering coefficient, $\mu_s'$, measured with the procedure described in, similar to that of biological tissue. The excitation mask used for the experiments divides the excitation light into many unit areas (approximately 1 mm$^2$), within each is embedded a small unilluminated area. This pattern is a "Dark Spot". The LSS signal for a unit area is the average spectrum of the lighted area minus that of the dark spot (Equation 1). FIG. 8a demonstrates the effectiveness of spatial gating. The black solid line is the total reflectance spectrum measured from the illuminated area, $I_{light}$. The reflectance spectrum from the neighboring local dark area ($I_{dark}$, dotted black line) contains only the diffuse reflectance component. The difference between the two spectra, $I_S$, is shown by the solid blue line. FIG. 8b is a close up of $I_S$ (solid line) and the best fit simulated result (dotted line).

Dark spot size is important because utilizing a smaller spot will reduce the unwanted blue photons of FIG. 7 and permit more lighted area, where single scatterings occur. Spot size is limited by our system's resolution, which is determined by the small collection numerical aperture (NA) intrinsic to angle dependent LSS measurements. This places a lower limit on the dark spot size of roughly diameter=50 μm. For DRS and IFS measurements, we use a "Light Spot" pattern as the mask. Light Spot is the inverse of Dark Spot, in that each unit area has a small illuminated region. This mimics a bundle of fastEEM contact-probes.

Measurements indicate spatial gating is a viable technique for separating the light scattering and diffuse reflectance components of the total reflectance spectrum. This complements the mathematical modeling used by the TMS fastEEM and polarization gating.

Angular gating is a gating technique capable of favoring single scattering from certain size scatterers over that from other sizes. It is implemented by collecting single backscattering at certain angles corresponding to favored sizes.

Figures 9A, 9B:
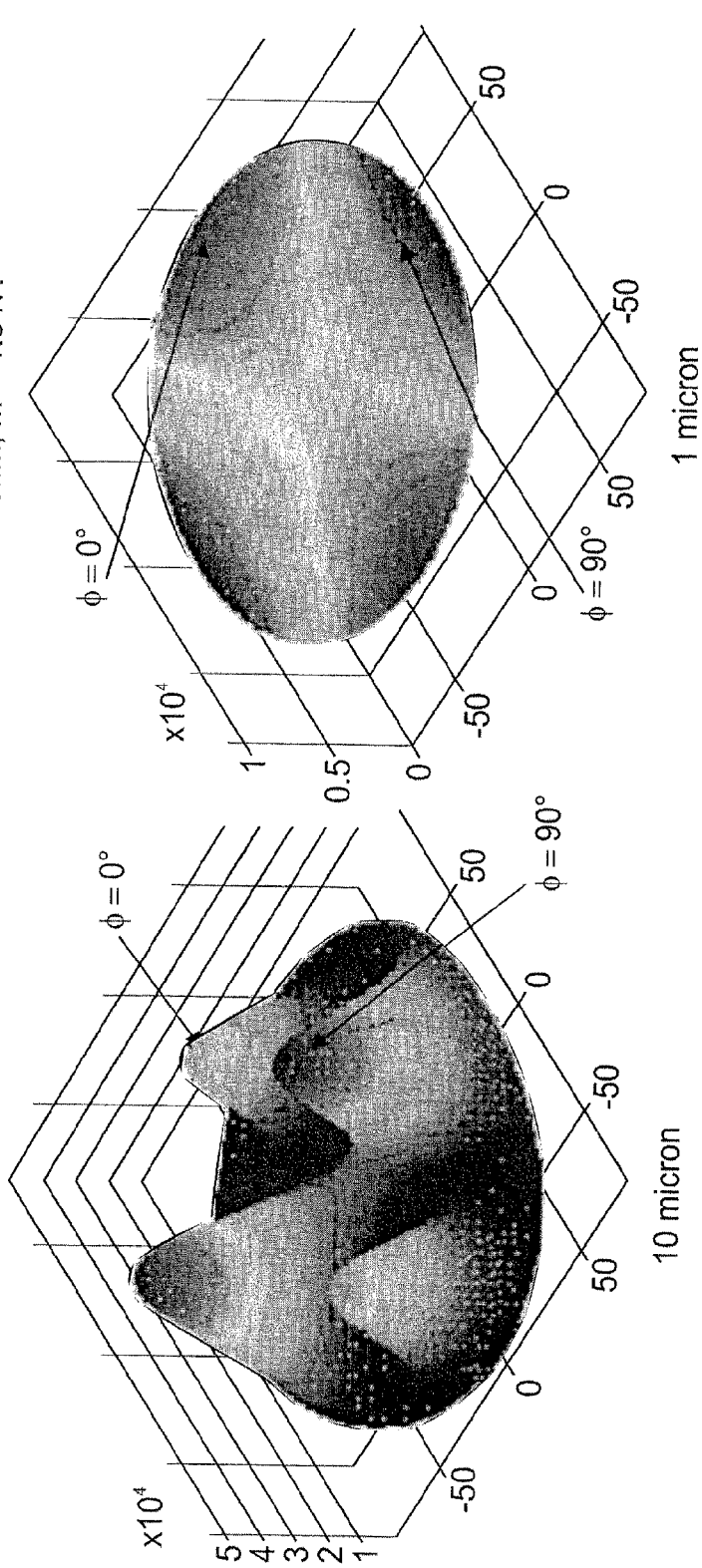
FIGS. 9a and 9b are angular scattering maps.
Figure 10A:
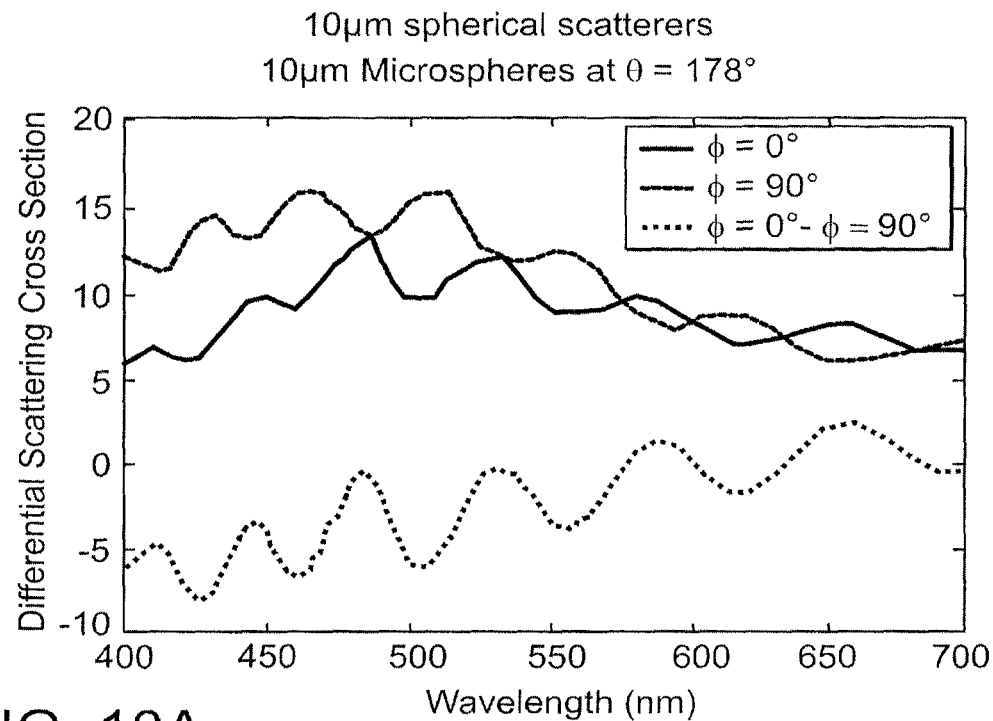
FIGS. 10a and 10b show spectral intensity variation for 10 and 1 micron spheres.
Figure 10B:
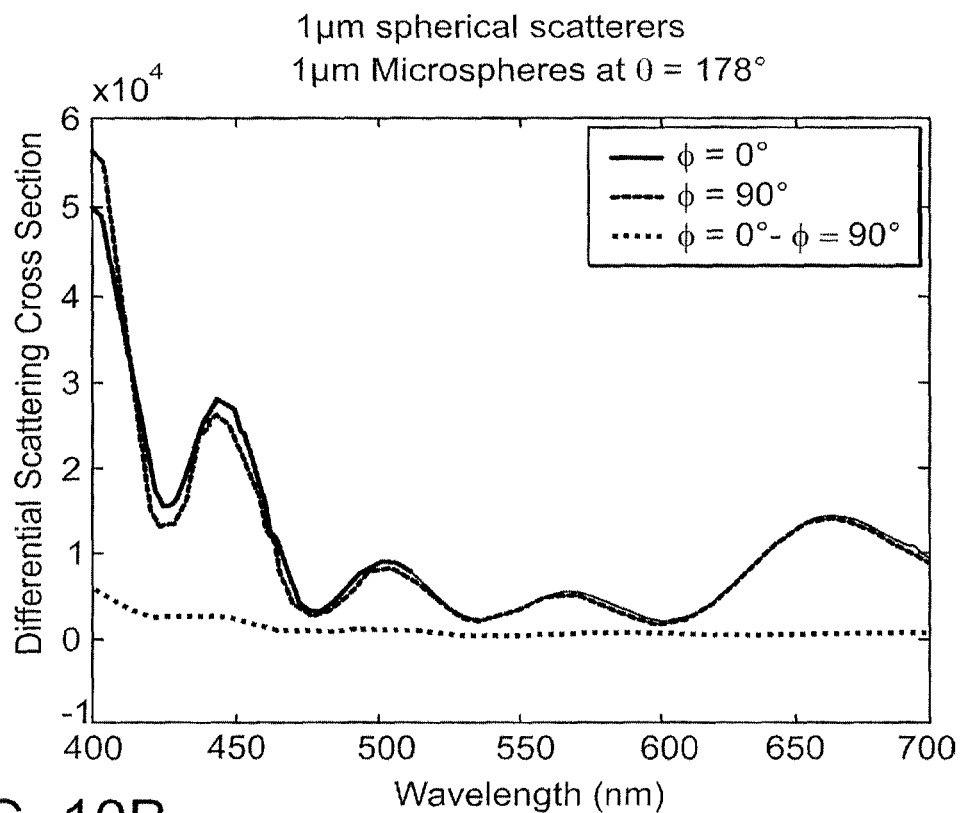

Angular gating exploits the non-isotropic scattering of large particles. The scattering intensity from a particle illuminated by a plane-wave is a function of scattering angle (θ), azimuthal angle (Φ), particle radius (a), light wavelength λ, and the relative index of refraction of the particle with its surrounding medium (m). FIG. 9 shows angular scattering maps of two different size scatterers. The radial direction corresponds to backscattering angle θ while the angular direction is Φ. Observe the 10 μm particle scatters in distinct lobes while the smaller 1 μm scatters isotropically. FIG. 10 shows the spectral plots of FIG. 9's Φ=0° and Φ=90° lobes. Note that the two 10 μm scattering spectra are very different while the 1 μm ones are almost identical. When one takes the difference between two spectra, the oscillatory feature is enhanced for 10 μm particles but suppressed for 1 μm particles. Based on this finding, Size Discrimination Angular Gating (SDAG), which produces a spectrum by taking the difference between Φ=0° and Φ=90° measurements. Implement SDAG by measuring two spectra. First, we set the excitation polarizer, P1 of FIG. 5, parallel to the surface of the table. P2 is set parallel to P1 and one full spectrum is recorded. Next, P1 and P2 are rotated 90° and another spectrum is recorded. Rotating the two polarizers is equivalent to moving 12 between the Φ=0° and Φ=90° positions on the fourier plane of L4. The difference of these two spectra will enhance the scattering signal from particles with certain sizes, chosen by the scattering angle θ.

SDAG: $I_{SDAG}(\lambda_i)=I(\lambda_i,\Phi=0°)-I(\lambda_i,\Phi=90°)$

To characterize SDAG, a microspheres sample with 10 μm, λ~0.2, and 1 μm, λ~2 immersed in the index matching solution used for calibration. The solution rests on top of an absorption neutral density filter. Scattering is measured at θ=178.1°, Φ=0° and Φ=90°. The peak backscattering lobes for 10 μm scattering are at these angles. Averaged results from the entire sample area are presented in FIG. 11a (Solid curves). Theoretical results (dotted curves) are computed using Mie Theory with the manufacturer's specifications for the 10 μm spheres because Angular Gating at θ=178.1° should discriminate against other sizes. $I_{SDAG}(\lambda_i)$ deviates little from the theoretical 10 μm spectrum despite a 10:1 optical density ratio between 1 μm and 10 μm microspheres. We also test the effectiveness of Angular Gating under increasing optical density ratios. FIG. 11b has ratio of 20:1, yet the 10 μm frequency is visible in $I_{SDAG}(\lambda_i)$.

Light scattering from tissue is composed of nuclei and smaller organelles scattering. Part of current precancer diagnosis relies on fitting the light scattering spectrum to a size distribution and index of refraction. Angular Gating favors certain size scatterers over others in the LSS spectrum, potentially allowing more accurate size distribution and index of refraction extraction. The respective scatterer sizes were used in the measurements because 10 μm approximates nuclear diameter while 1 μm approximates mitochondria diameter, one of the more abundant smaller organelles. In squamous and columnar epithelial cells, the optical density ratio between mitochondria and nuclei is approximately 10:1, as estimated from. Measurements have demonstrated successful size discrimination under similar conditions. Size Discrimination Angular Gating can significantly enhance the nuclear signal in LSS.

A TMS imaging instrument is used for detecting cervical dysplasia, oral cavity dysplasia, and breast lesions. Images are collected by simultaneously collecting image data with a two-dimensional spatial array of pixel elements to collect light from a corresponding area of a tissue surface. Preferably, the imaging detector has at least a 500×500 array of pixel elements. Such an image of the region of interest is collected for each of the fluorescence and reflectance images used in the system. In a preferred embodiment separate light sources can be used for the fluorescence and reflectance images, the light from each source being delivered through a common light delivery system, with the images being collected through at least a partially common light path of the light collection systems.

Figure 12:
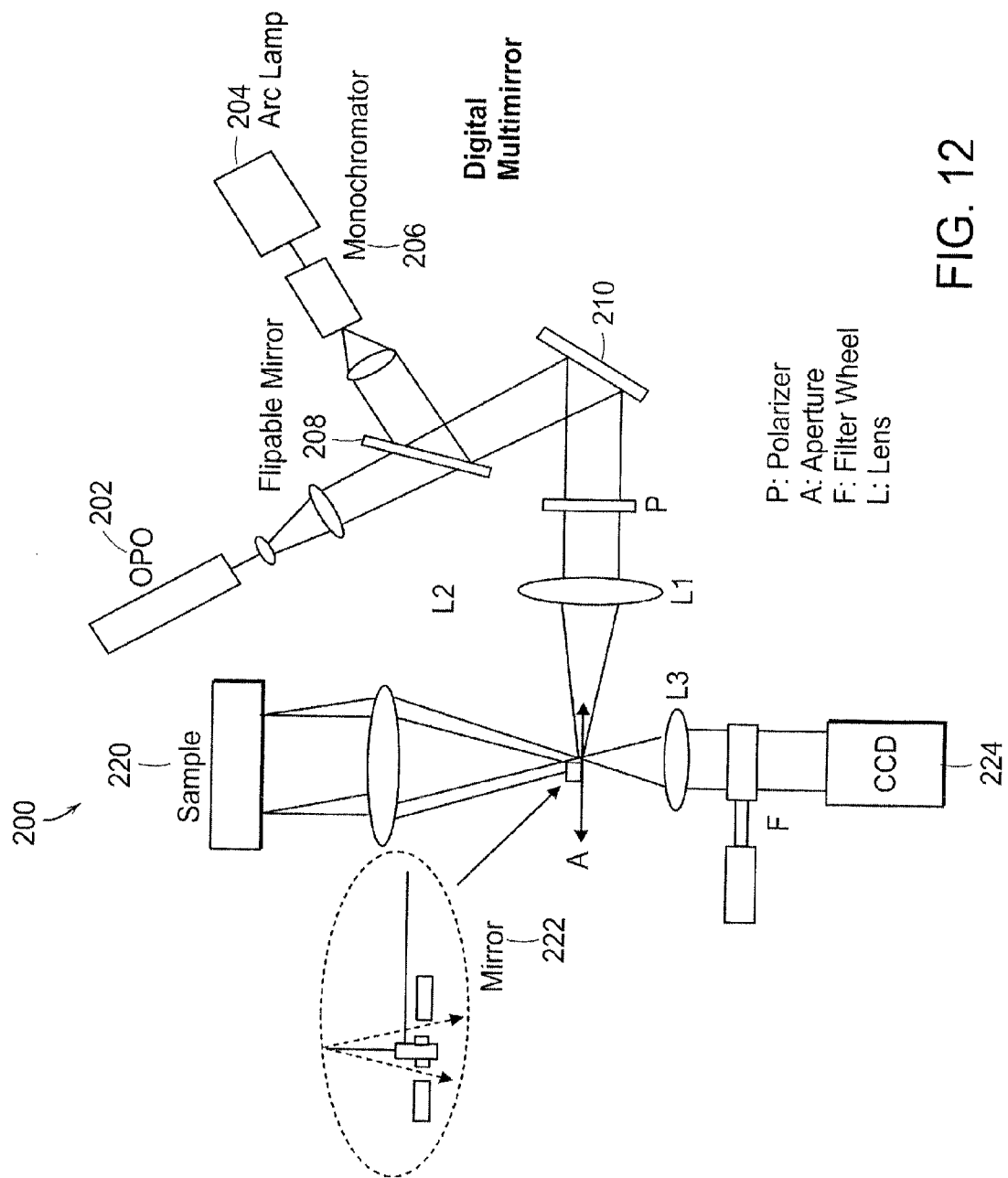
FIG. 12 is a further preferred embodiment of an imaging system.

The system includes studying LSS, DRS, and IFS in the imaging mode, the spatial and angular gating techniques. Table 4 shows the requirements for LSS, DRS, and IFS measurements. To achieve these objectives, the system 200 is displayed in FIG. 12 For LSS data acquisition, a wavelength tunable optical parametric oscillator 202 (OPO) is used to provide single wavelength excitation from 400-700 nm. The OPO allows 2 orders of magnitude increase in excitation power on the sample over the Xenon Arc Lamp 204 due to its better collimation, which leads to stronger light scattering signals when exposure time is constrained. The wavelength tuning speed of the OPO is also higher than that of the monochromator 206. This further expedites data collection and avoids cell or ex-vivo tissue degradation problems during measurements. During data acquisition, light from either the OPO or the arc lamp is selected to excite the multimirror 210 by a flippable mirror 208. The digital multimirror device (DMD, Texas Instruments) is a 1024 pixel×768 pixel array of micromirrors which can be separately directed at two different angles. Each mirror pixel is estimated to be 14 microns by 14 microns. The DMD acts as a spatial light modulator and is used to define precise excitation patterns. For LSS, a dark spot pattern of excited light reflected by the multimirror is imaged and magnified 1:2 onto the sample by L1 and L2. Polarizer P defines the excitation polarization. The beamsplitter and I1 of FIG. 5 are replaced by a mirror, <3 mm diameter, placed at the focal point of L1, L2, and L3. This mirror serves 2 purposes: it defines the divergence of the excitation and redirects the light towards the sample. With L2 focal length of 16 cm, the excitation divergence is limited to a half angle of 0.5° which leads to spatial resolution of approximately 50 μm. Light scattered from the tissue 220 not at scattering angle θ between 179° and 181° will miss the mirror 222 during collection and be imaged onto the CCD 224 by L2 and L3. Aperture A around the mirror defines the ranges of θ's and Φ's permitted to pass through to L3. The aperture is opened to permit ±0.5° about the desired θ and Φ. For DRS data acquisition, a Xenon arc lamp and monochromator are used to provide single wavelength excitation from 300-700 nm. Light propagates through the system as in LSS, except the multimirror reflects a light spot pattern and aperture A is removed to collect as much reflectance as the lenses will permit. For IFS data acquisition, the arc lamp and monochromator provide single wavelength excitation from 300-400 nm. Light propogates through the system as in DRS, except the narrow line width filters, F, are rotated with each image acquired to define collected light wavelength.

Data acquisition and processing will be automated by a computer program written on Labview 7.0 (National Instruments). Algorithms are adapted from those used in the fastEEM.

TABLE 4

Requirements for LSS, DRS, and IFS measurements

| | LSS | DRS | IFS |
|---|---|---|---|
| Excitation wavelength | 400-700 nm | 300-700 nm | 300-400 nm |
| Excitation collimation | ±0.5 degrees | N/A | N/A |
| Mask type | Dark Spot | Light Spot | Light Spot |
| Polarized Excitation required | Yes | no | no |
| Collection collimation | ±0.5 degrees | N/A | N/A |

The imaging instrument is constructed from optimal implementations and specifications tested on the TMS fastEEM. It is used for real time wide-area studies of uterine cervix, oral cavity, esophagus, and breast.

Figure 13:
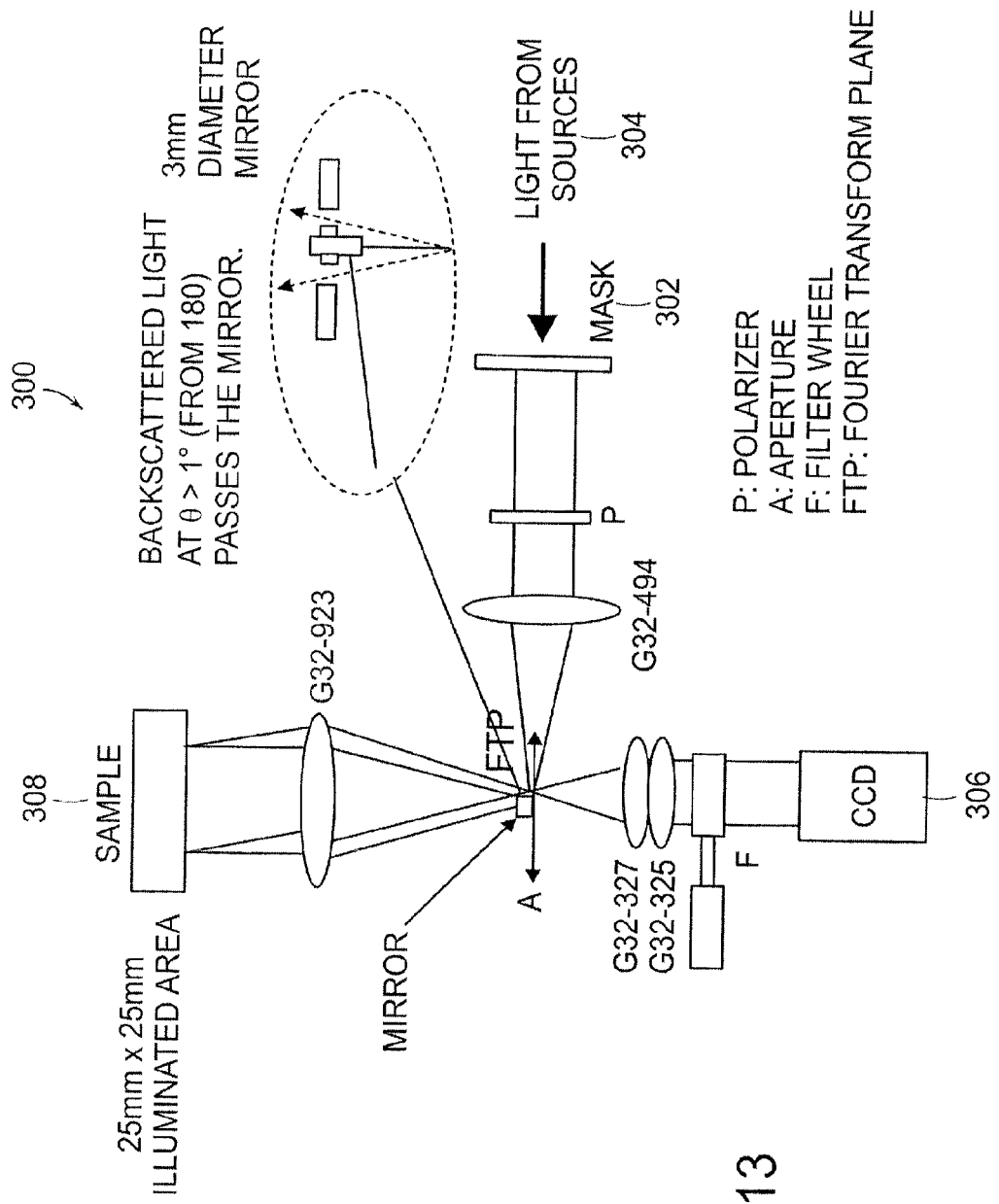
FIG. 13 is another preferred embodiment of an imaging system.

The system's 300 optics are arranged as illustrated in FIG. 13 to meet the TMS requirements on Table 4. The optical setup and data acquisition software are similar to those of the prior system. The multimirror is no longer used as the excitation mask. Instead, a dark spot pattern mask 302 for LSS is made of glass with opaque dots. For DRS and IFS light spot masks, light from the arc lamp 304 into the proximal end of a fiber bundle. The distal end is attached to the source plane to form the light spot pattern. These changes improve transmission efficiency and reduce complexity. A wheel of narrow linewidth filters replaces the monochromator because filters scan the spectrum much faster. The CCD 306 is set to high sensitivity for IFS data acquisition because speed is important. The distance from lens G32-923 (Edmund Optics) to the sample 308 is roughly 15 cm. The collection optics, with the aperture between lenses G32-923 and G32-327 fully opened, can have F number approximately 4.

LSS measurements with a dark spot mask use more power. A typical megapixel CCD has a well depth of 100000 photoelectrons/pixel and quantum efficiency 50%. To maximize signal to noise ratio, there are approximately 200000 photons/pixel on the CCD. For LSS measurements, scattered light reaches the CCD only if is within ±0.5 degrees of the measured θ. Therefore, if we assume the tissue is a Lambertian scatterer, a good approximation for diffusive media like tissue, roughly $2.5 \times 10^{15}$ photons are needed to exit the tissue. This corresponds to about 1 mJ of energy spread over the entire area (4 cm$^2$) at every wavelength measured. The excitation light must be collimated to ±0.5 degrees and have relatively narrow line width (~10 nm). Between the excitation mask carrying the dark spot pattern and the sample, the light passes through a linear polarizer P. This cuts energy by roughly 60%. Therefore, about 3 mJ is needed from monochromatic, collimated light illuminating the mask. The OPO emits 30 mJ/pulse (5-8 ns pulse, 1 nm line width) in the visible regime and operates at 20 Hz. Assuming efficient light transmission from the laser to the mask via a fiber, one pulse provides enough power for one LSS image. DRS and IFS measurements can be acquired with a Xenon arc-lamp. Based on the power requirements of a fastEEM contact-probe, this light source provides ample energy for DRS. For IFS however, use the high sensitivity mode of the CCD is used because IFS signals pass through a narrow line width filter. The OPO system, a 300W Xenon arc lamp, and a PhotonMax CCD (Princeton Instruments) meet the requirements.

The total data-acquisition time depends on the number of measurement images required and light source wavelength scan speed. A preliminary estimate can be based on spectral features. The key features of the DRS spectrum are the hemoglobin absorption dips and the slope. We estimate 12 points placed about the Hb dips can adequately characterize the spectrum. A total of one DRS spectrum is required. The IFS spectra have peaks at emission wavelengths corresponding to NADH, tryptophan, collagen, FAD, and porphyrin. An estimate 11 emission wavelengths can characterize the spectrum for each excitation wavelength. 3 excitation wavelengths at 308 nm, 340 nm, and 400 nm have high diagnostic value. For LSS spectra, wavelengths were measured for each polarization gating setting. However, the speed of data acquisition is limited by the OPO wavelength sweep speed, which is 3 seconds from 400 nm to 700 nm. In total, TMS imaging will take approximately 160 images. LSS data can be acquired in 6 s. IFS can be acquired in 2 s and DRS in 1 s. The PhotonMax has frame rate >25/s, so image acquisition is not a limiting factor. To decrease acquisition time, we will investigate laser systems that cannot emit at as many excitation wavelengths as the OPO, but can scan the spectrum from 400-700 nm faster because we do not require 60 images/LSS spectrum.

The TMS imaging system can be used for two purposes: (1) as a diagnostic tool to detect, diagnose, characterize and (2) to guide biopsy of dysplastic intraepithelial lesions. Because this instrument allows early dysplastic transformation to be characterized without the need for tissue removal, it enables the natural history of such lesions to be studied in vivo.

TMS imaging operates like a bundle of many TMS contact-probe systems for DRS and IFS. One fastEEM contact-probe can analyze roughly 1 mm$^2$ of tissue, so a bundle of several hundred can simultaneously analyze a few cm$^2$ of tissue. TMS imaging illuminates the tissue with a number of light spots and collects the reflectance from the area around each spot. Each light spot and the signals collected around it are similar to a fastEEM probe. TMS imaging results are comparable to the successful results from single point TMS, but there are differences in the comparison that need to be considered. A contact probe excites and collects reflectance from the tissue with larger acceptance angle than the imaging system. As a result, the imaging system has better angular resolution, crucial for LSS, but requires more excitation power to collect equal reflectance. Spectral information cannot be acquired in one image because the CCD's pixels record spatial information. Therefore, multiple images, each at a different wavelength, are required. This increases acquisition time. When multiple light spots excite the tissue simultaneously, excitation from one spot can enter the detection area of another spot. This is cross talk, which hinders acquisition of local reflectance information.

To minimize unwanted multiple scatterings and enhance LSS signal, limits of dark spot size are modified to reach the resolution limit, which was roughly 50 μm. The effectiveness of different dark spot shape and spacing. The main challenge for optimizing the dark spots is designing accurate and precise masks. For example, changing dark spot size, shape, or spacing all require etching a mask.

Size Discrimination Angular Gating can be evaluated by progressively increasing 1 μm optical density and measuring clarity of the favored 10 μm spectrum at θ=178°. The effects of size, angle and index of refraction distributions on technique effectiveness. SDAG measurements are used with different scatterer sizes at their optimal angles and with varying degrees of excitation collimation. The results of these measurements will demonstrate the strengths and limitations of angular gating. Data acquisition time with the clinical system can be reduced if relaxing excitation collimation minimally influences results.

To effectively measure diffuse reflectance contribution from one region of the sample, the "Dark Spot" excitation pattern requires modification because the red photons of FIG. 7 detected in one area originated from multiple origins. This is cross talk.

For a point source excitation on a homogeneous medium with scattering and absorption coefficients $\mu_s'$ and $\mu_a$, Farrell et. Al derived the diffuse reflectance flux perpendicular to the surface at different distances ρ from the source to be:

$$R(\rho) = \frac{z_0 a'}{4\pi}\left[\left(\mu_{\mathit{eff}} + \frac{1}{r_1}\right)\frac{e^{-\mu_{\mathit{eff}} r_1}}{r_1^2} + \left(1 + \frac{4}{3}A\right)\left(\mu_{\mathit{eff}} + \frac{1}{r_2}\right)\frac{e^{-\mu_{\mathit{eff}} r_2}}{r_2^2}\right]$$

The symbols are defined as:

$$r_1 = [z_0^2 + \rho^2]^{\frac{1}{2}}$$

$$r_2 = \left[\left(z_0\left(1 + \frac{4}{3}A\right)\right)^2 + \rho^2\right]^{\frac{1}{2}}$$

$$a' = \frac{\mu_s'}{\mu_a + \mu_s'}$$

$$\mu_{\mathit{eff}} = \sqrt{3\mu_a(\mu_a + \mu_s')}$$

$$z_0 = \frac{1}{\mu_a + \mu_s'}$$

This assumes all scattering events are isotropic. Parameter A depends on the refractive index of the medium and is roughly 3.2 in colon tissue. Assume the medium is human tissue and its entire surface is illuminated by excitation light. With this assumption even though imaging systems have finite illumination areas to achieve a closed-form solution. The total diffuse reflectance flux perpendicular to the tissue is given by:

$$R = \int_0^{2\pi} d\theta \int_0^{\infty} R(\rho)\rho d\rho = \left(1 + e^{-\frac{4}{3}A\mu_{\mathit{eff}} z_0}\right)\frac{e^{-\mu_{\mathit{eff}} z_0}}{2}$$

The desired tissue parameters $\mu_s'$ and $\mu_a$ appear in $\mu_{\mathit{eff}}*z_0$. The above equation can only be solved for $\mu_{\mathit{eff}}*z_0$ and not the desired parameters $\mu_s'$ and $\mu_a$ separately. This is not a problem for single point systems. To address cross talk, we use a form of spatial gating where the excitation pattern is again divided into many unit areas, but instead of dark spots, each area has a "Light Spot". The local diffuse reflectance spectrum is the average spectrum in the area. The size of a unit area is set such that diffuse reflectance recorded in the area comes largely from the local light spot. The illuminated spot is made as small as physically possible. IFS imaging may also encounter some cross talk difficulties because it is extracted using the reflectance spectrum. By adjusting the size of the unit areas with tissue phantoms containing scatterers and fluorophores to minimize residual cross talk. The influence of light spot shape and spacing can be addressed.

Non-contact DRS and IFS imaging collects reflectance with a smaller acceptance angle than single point systems. This immediately increases data-acquisition time, but may also influence spectral features. Different acceptance angles can influence reflectance and fluorescence spectra. By varying collection angle in the system and by adjusting the collection aperture these can be addressed.

Gating techniques can be used with tissue phantoms and the system has demonstrated successful separation of LSS and DRS and effective discrimination of scatterer size.

The TMS imaging system is used to detect precancer and early cancer in the cervical and oral cavities. The extracted tissue biochemical and morphological information is compared to histology and correlated with pathology.

Cell rafts will have oral cells, grown from biopsied tissue, supported by a layer of collagen. The raft is immersed in growth media up to the level of the cells. We will create rafts with normal or malignant cells. Cell rafts can be used for oral cancer imaging measurements on both normal and cancerous samples.

Within an improved fitting algorithm that minimizes the least square error between fit and LSS data with minimal assumptions for tissue parameter extraction. This forms the LSS portion of the real-time data processing algorithm in the clinical system. The method of was sensitive to noise because uncertainty often appeared as oscillatory features. The method of assumed a Gaussian distribution. The Mie Theory Fitting Algorithm, MTFA, will solve the optimization problem $\min\|Ax-b\|_{x\geq 0}$. Parameter A is a matrix of scattering intensities computed at different sizes, wavelengths, angles, and index of refractions using Mie Theory. Parameter b is an experimentally recorded spectrum and x is the best fit size distribution. Our assumptions are uniform scattering angle, index of refraction, and $x \geq 0$. Unfortunately, non-linear constraints greatly increase computation time. MFTA is optimized to reject experimental noise and reduce computation time. DRS and IFS data processing algorithms have been developed for the fastEEM and are adapted to the TMS imaging system.

The instrumentation and diagnosis algorithms analyze the data. The organs are uterine cervix, oral cavity, esophagus, and breast. The imaging system is less invasive than the TMS fastEEM studies because no physical contact is required.

With one button press, the first generation system will acquire LSS, DRS, and IFS measurements in under 10 s. Short data acquisition time makes it easier for the patient to remain motionless. The doctor will mark regions in the data acquisition area for biopsies. The results are spatially correlated with wide area spectroscopic measurements. The system provides a precancer diagnostic tool for cervix and oral cavities. The user presses a button to begin data acquisition, which finishes within 2 seconds. Then, rapid data processing produces a diagnostic map that color codes precancer risk and displays on the computer screen. Therefore, the user can see in real time which areas are at greater risk for precancer. The method correlates spectroscopy diagnosis with pathology analysis and can guide biopsy or papa smears.

Figure 14:
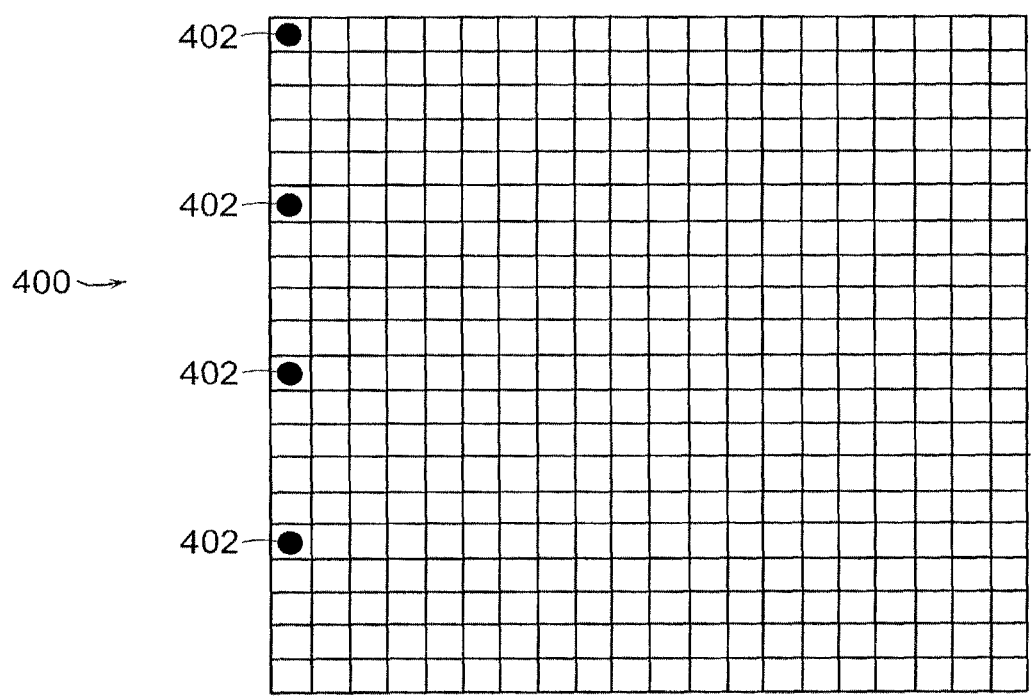
FIG. 14 illustrates a scanning spot pattern used for imaging a region of interest.

The imaging can be conducted in multiple shots. For each shot, four collinear light spots illuminate four of the diagnostic regions on the tissue surface and reflectance spectra from these regions are imaged onto the CCD via a spectrograph. The four light spots 402 are shown on FIG. 14. To cover the entire area 400, the line of spots is scanned across the tissue surface.

Figure 15:
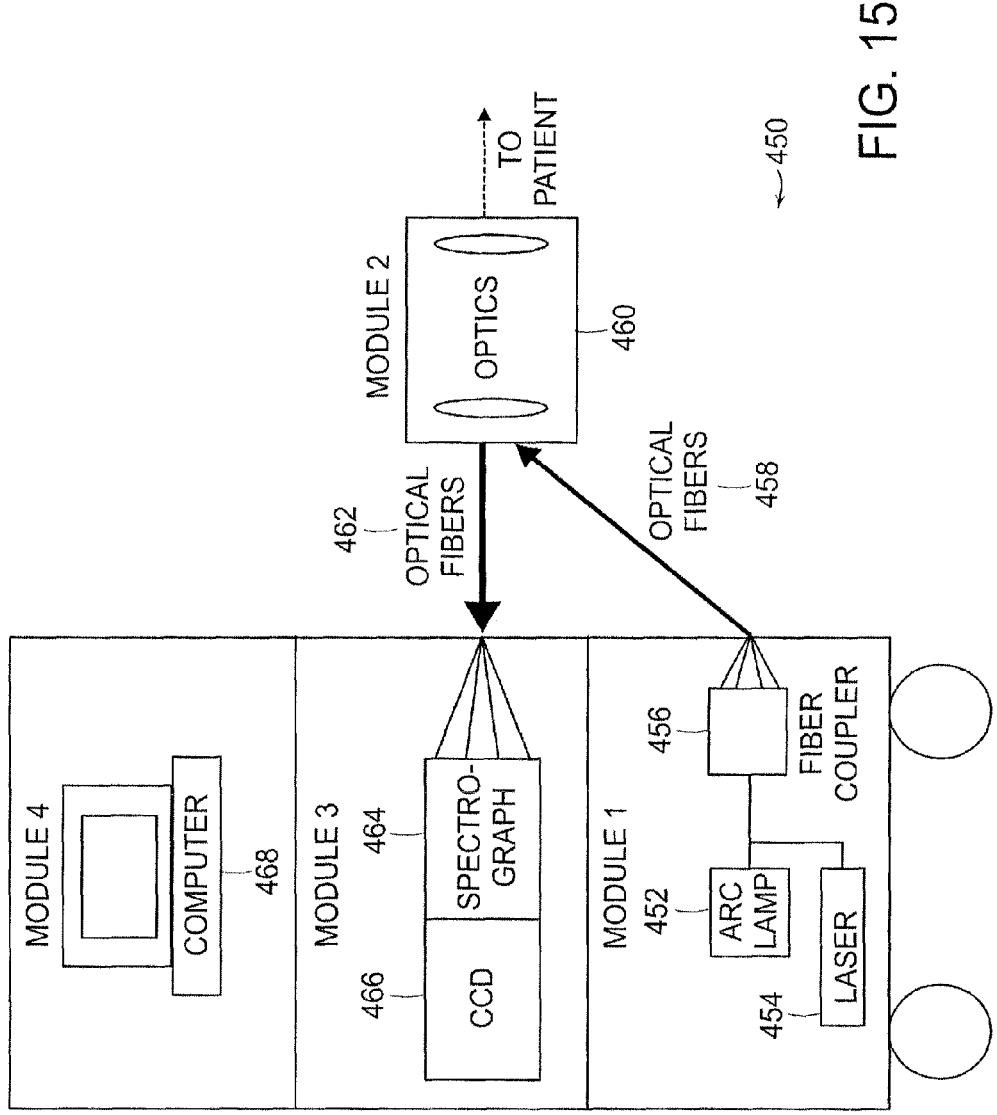
FIG. 15 illustrates a portable system for use with a preferred embodiment of the invention.

A general layout of the TMS imaging system 450 for cervix and oral cavity studies, for example, is shown in FIG. 15, along with critical requirements. Module 1 houses a broadband white light source 452 and a 340 nm nitrogen laser 454, along with a coupler 456 to couple light into four delivery fibers 458. The fibers are bundled together to deliver light from Module 1 to Module 2, which is a compact and light-weight handheld unit containing the system optics. At the input end of Module 2, the fibers' distal ends are aligned collinearly. A bundle of 8 collection fibers 462 transfers light from Module 2 to Module 3, which houses the spectrograph 464 and CCD 468. Module 4 houses the computer 468 and software for instrument control and data processing. Modules 1, 3 and 4 will be placed on a mobile, compact cart suited for hospital settings.

TABLE 5

Constraints for Module 2

| | |
|---|---|
| Size | No larger than a single lens reflex camera. |
| Weight | Less than 5 lbs. |
| Separation between instrument and patient | 15 cm to 30 cm variable (maybe closer in the oral cavity) |
| Sampling | Four approximately 0.6 mm diameter white light spots illuminate the tissue. These spots are arranged collinearly and spaced 5 mm apart. |
| Collection angle | $2° \pm 0.5°$ from the direct backscattering direction and at azimuthal angles $\phi = 0°$ and $\phi = 90°$. |
| Sweeping | The line of light spots must be swept across the patient to cover a 2 cm × 2 cm area with resolution no larger than 1 mm × 1 mm. Each unit area yields a diagnosis. |
| Light wavelength (Fluorescence) | 340 nm excitation 370 nm-700 nm collection |
| Light wavelength (Elastic scattering) | 370 nm-700 nm illumination 370 nm-700 nm collection |
| Image acquisition time | <10 s. |
| Focus | Due to the uneven nature of the tissue surface, some regions of the 2 cm × 2 cm area will be in focus while other regions will be out of focus. Focus should be corrected either by moving components within the system (autofocus?) or by data processing after all data has been acquired. |

TABLE 6

Additional constraints for combined Modules 2/3

| CCD | |
|---|---|
| Quantum Efficiency | >50% from 370 nm -700 nm |
| Readout rate | >10 frames/s |
| Chip size | >=8 mm × 8 mm |
| Pixel number | >=512 × 512 |
| Full well | >=100ke$^-$ |
| Dark current | <0.1 e$^-$/pixel/sec @ operating temperature |
| Spectrograph | |
| Range | 370 nm-700 nm on the corresponding CCD |
| Line width | FWHM <= 10 nm on the corresponding CCD |

TABLE 6-continued

Additional constraints for combined Modules 2/3

| Efficiency | >50% over wavelength range |
|---|---|
| Slit height | >=1 cm |
| Acceptance F/# | <=4 |

Figure 16:
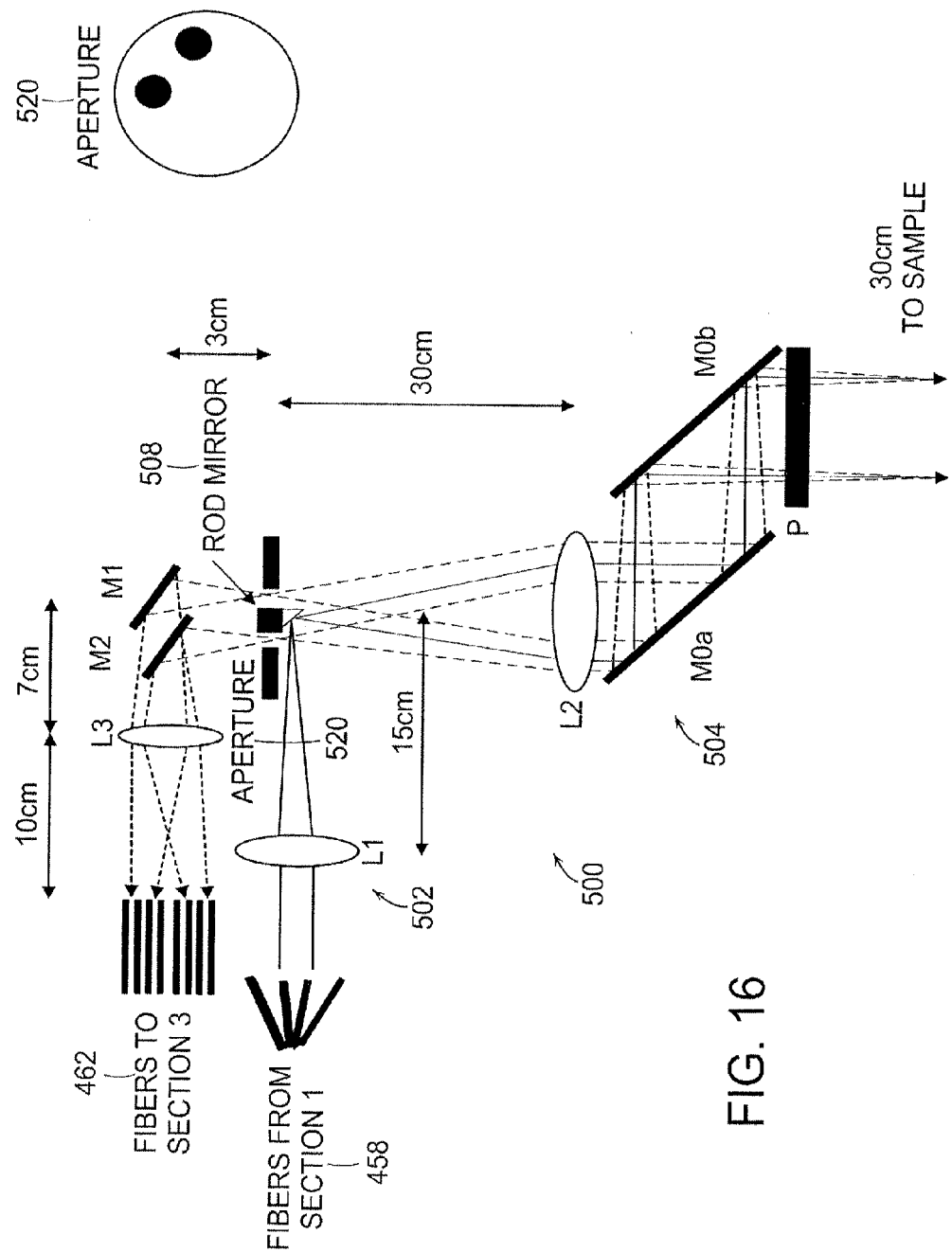
FIG. 16 shows a schematic of a system for use in a handheld probe.

FIG. 16 illustrates a preferred embodiment of a system 500 of the inside of Module 2. This includes a handle 502 and a distal probe 504 for insertion into body cavities. Light delivered from Module 1 is focused by lens L1 (f=15 cm) onto a 5 mm diameter rod mirror. The chromatic aberration of L1 is sufficiently small in the wavelength range of the system, 340 nm-700 nm, such that the light is able to focus onto the rod mirror 508. L2 (f=30 cm) collimates the light onto mirror M0a. L2 must also experience minimal chromatic aberration from 340 nm-700 nm. M0a and M0b redirect the light to the patient. The focal lengths of L1 and L2 can vary, but the pattern of light delivered from Module 1 must be imaged onto the tissue, which is a fixed 30 cm from M0b. M0a and M0b can be adjusted to sweep the line of spots across the tissue surface. Light returning from the tissue travels through M0a, M0b and L2. Two solid angles of light centered at $\theta=2°$, $\phi=0°$ and $\phi=90°$, are permitted to pass by the aperture 520 through to M1 and M2. The aperture is located one focal length behind L2. The two cones of light passing through the aperture are redirected by M1 and M2 towards L3 (f=10 cm). M1 and M2 separate the two beams slightly such that L3 will form two separate images of the line of spots. Each of the 8 images of the original 4 spots of light is coupled into a fiber that delivers light to Module 3.

In FIG. 16 M indicates mirrors, P indicates linear polarizers, and L indicates lenses. The blue and red rays are the $\phi=0°$ and $\phi=90°$ rays respectively. In this figure, M2 appears to obstruct the light path off M1. M2 and M1 are positioned in different planes such that no obstruction occurs. The aperture in the top right corner is a expanded view of the aperture in the system. The top hole permits the $\phi=0°$ ray to pass and the right hole permits the $\phi=90°$ ray to pass.

Folded beams are used to reduce the size of the system to provide a handheld probe. Modules 2 and 3 are integrated into a single unit while respecting size and weight requirements.

While the present invention has been described herein in conjunction with a preferred embodiment, a person with ordinary skill in the art, after reading the foregoing specification, can effect changes, substitutions of equivalents and other types of alterations to the system and method that are set forth herein. Each embodiment described above can also have included or incorporated therewith such variations as disclosed in regard to any or all of the other embodiments. Thus, it is intended that protection granted by Letters Patent hereon be limited in breadth only be definitions contained in the appended claims and any equivalents thereof.

What is claimed is:

1. A spectroscopic imaging system comprising:
a light source system including a broadband light source and a laser light source for inducing tissue autofluorescence;
an optical scanning system configured to optically couple light from the light source system across a scanning region that is positioned to receive scanning light that is incident on an illumination area within the scanning region, the optical scanning system including a moveable mirror device;
a fiber optic device optically coupling light from the light source system to the optical scanning system, the fiber optic device having a proximal end and a distal end;
an imaging detector optically coupled to a proximal end of the fiber optic device such that the imaging detector detects autofluorescent light and reflectance light to provide autofluorescence image data and reflectance image data;
the moveable mirror device providing relative movement between light emitted from a distal end of the fiber optic device and the scanning region, the optical scanning system optically coupling light received from the scanning region by the moveable mirror device into a plurality of collection optical fibers of the fiber optic device, the proximal end of the plurality of collection optical fibers being optically coupled to the imaging detector for acquiring images of tissue; and
a data processor connected to the imaging detector that processes the autofluorescence image data and reflectance image data to generate a diagnosis.

2. The system of claim 1 further comprising a mask positioned between the light source system and the scanning region and a plurality of filters to filter collected light.

3. The system of claim 1 wherein the moveable mirror device is optically coupled to the distal end of the fiber optic device.

4. The system of claim 3 wherein the movable mirror device comprises a digital micromirror array.

5. The system of claim 1 further comprising a computer program stored in a memory and operating on the data processor, the computer program processing the autofluorescence image data and the reflectance image data to compute intrinsic autofluorescence data and diffuse reflectance data.

6. The system of claim 1 wherein the broadband light source comprises a tunable source.

7. The system of claim 1 wherein a flipping movable mirror switches between the broadband light source and the laser light source.

8. The system of claim 1 wherein the light source system includes an optical parametric oscillator.

9. The system of claim 1 further comprising a spatial gate positioned between the scanning region and the imaging detector.

10. The system of claim 1 further comprising an angular gate positioned between the scanning region and the imaging detector.

11. The system of claim 1 wherein the data processor determines a size of a cellular structure from a reflectance spectrum.

12. The system of claim 1 wherein the fiber optic device is optically coupled to an aperture that collects the autofluorescence light and reflectance light.

13. The system of claim 1 wherein the detector simultaneously detects an area of a region of interest with a two dimensional array of pixel elements such that the scanning system images adjacent regions in sequence.

14. The system of claim 1 wherein the detector comprises at least a 500×500 array of pixel elements such that the detector generates an image of an area of the scanning region having at least 500×500 image pixels.

15. The system of claim 1 wherein the system further comprises a polarizer such that the collection optical fibers couple polarized light to the imaging detector.

16. The system of claim 1 further comprising a polarizer positioned between the scanning region and the imaging detector.

17. The system of claim 1 further comprising an aperture positioned between the scanning region and the collection optical fibers that separates a polarization component.

18. The system of claim 1 wherein the light source system emits light at a plurality of different wavelengths that are coupled to the optical scanning system such that the imaging detector detects separate images at each of the plurality of different wavelengths.

19. The system of claim 18 further comprising a polarizer and an aperture such that at least one polarized light component is coupled to the collection optical fibers.

20. The system of claim 1 wherein the fiber optic device comprises a plurality of light delivery optical fibers that are optically coupled to the moveable mirror device that simultaneously scans different regions of tissue with a plurality of light spots.

21. The system of claim 1 wherein the fiber optic device comprises illumination optical fibers and the plurality of collection optical fibers.

22. A spectroscopic imaging system comprising:
a light source system including a broadband light source and a laser light source for inducing tissue autofluorescence;
an optical scanning system that is configured to optically couple scanning light from the light source system across a scanning spot pattern, the optical scanning system including a moveable mirror device;
a fiber optic device optically connecting the light source system to the optical scanning system;
an imaging detector optically coupled to a proximal end of the fiber optic device such that the imaging detector detects autofluorescent light and reflectance light to provide autofluorescence image data and reflectance image data;
the moveable mirror device providing relative movement between light emitted from a distal end of the fiber optic device and a scanning region defined by an illumination area of the scanning spot pattern to simultaneously deliver a plurality of separated light spots that are scanned across the scanning region, the moveable mirror device optically coupling received light from the scanning region into a plurality of collection optical fibers of the fiber optic device, a proximal end of the collection optical fibers being optically coupled to the imaging detector to acquire images; and
a data processor connected to the imaging detector that processes the autofluorescence image data and reflectance image data to generate a diagnosis.

23. The system of claim 22 wherein the moveable mirror device is optically coupled to a distal end of the collection optical fibers.

24. The system of claim 22 further comprising a computer program stored in a memory and operating on the data processor, the computer program processing the autofluorescence image data and the reflectance image data to compute intrinsic autofluorescence data and diffuse reflectance data to generate a diagnosis of a cancerous condition.

25. The system of claim 22 further comprising a spatial gate or an angular gate positioned in an optical path between the moveable mirror device and the collection optical fibers that are coupled to the imaging detector.

26. The system of claim 22 wherein the fiber optic device further comprises a plurality of spaced illumination optical fibers to couple light spots to the scanning optical system.

27. The system of claim 22 wherein the fiber optic device further comprises a plurality of illumination fibers that are optically coupled to the moveable mirror device wherein the scanning region is configured with a plurality of illumination areas such that each respective light spot is smaller than an area illuminated by each respective light spot, the scanning spot pattern defined by a line of spots.

28. The system of claim 22 further comprising a phantom having scatterers and fluorophores, the phantom being illuminated with light from the light source system such that light from the phantom is detected with the imaging detector and wherein the data processor processes the detected light to determine an illumination unit area of the scanning region.

* * * * *